US012775005B2

(12) United States Patent
Rao et al.

(10) Patent No.: US 12,775,005 B2
(45) Date of Patent: Oct. 27, 2026

(54) KETONE BODY SENSING DEVICE AND METHOD

(71) Applicant: MEDTRONIC MINIMED, INC., Northridge, CA (US)

(72) Inventors: Ashwin K. Rao, West Hills, CA (US); Rebecca K. Gottlieb, Culver City, CA (US); Quyen Ong, Arcadia, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 1753 days.

(21) Appl. No.: 17/025,999

(22) Filed: Sep. 18, 2020

(65) Prior Publication Data

US 2021/0003564 A1 Jan. 7, 2021

Related U.S. Application Data

(63) Continuation-in-part of application No. 15/912,473, filed on Mar. 5, 2018, now Pat. No. 11,986,288, and (Continued)

(51) Int. Cl.

*G01N 33/52* (2006.01)
*C12N 9/04* (2006.01)
*G01N 1/14* (2006.01)

(52) U.S. Cl.

CPC ......... *G01N 33/523* (2013.01); *C12N 9/0006* (2013.01); *G01N 1/14* (2013.01); *C12Y 101/0103* (2013.01); *G01N 2001/149* (2013.01)

(58) Field of Classification Search

CPC .... A61K 35/28; A61K 35/50; A61K 38/1825; A61K 38/1841; A61K 38/39; A61K 38/57; A61K 31/337; A61K 40/19; A61K 40/24; A61K 40/414; A61K 40/4205; A61K 2239/38; A61K 2239/47; A01N 1/0221; C12N 5/0605; C12N 2500/02; C12N 2501/115; C12N 2502/025; C12N 9/0006;

(Continued)

(56) References Cited

U.S. PATENT DOCUMENTS 4,562,751 A 1/1986 Nason et al.
4,685,903 A 8/1987 Cable et al.

(Continued)

FOREIGN PATENT DOCUMENTS

CA 3124578 A1 * 4/2015 ............ A61M 37/00
CN 101900734 A 12/2010

(Continued)

OTHER PUBLICATIONS

Non-Final Office Action dated Nov. 7, 2024 for U.S. Appl. No. 15/912,451.

(Continued)

*Primary Examiner* — Peter Paras, Jr.
*Assistant Examiner* — Lauren K Van Buren
(74) *Attorney, Agent, or Firm* — GATES & COOPER LLP

(57) ABSTRACT

Devices, patch sensors, and methods for detecting a ketone body are disclosed. An exemplary device includes a collection apparatus for collecting a sample amount of interstitial fluid and a ketone body indicator having an initial negative state and having a positive state when at least a threshold value of the ketone body is collected in the sample amount.

9 Claims, 6 Drawing Sheets

Related U.S. Application Data a continuation-in-part of application No. 15/912,451, filed on Mar. 5, 2018, now Pat. No. 12,635,915.

(60) Provisional application No. 62/467,653, filed on Mar. 6, 2017.

(58) Field of Classification Search
CPC .......... A61P 17/00; A61P 17/02; A61P 43/00; A61P 35/00; G01N 33/523; G01N 1/14; G01N 2001/149; G01N 33/64; G01N 33/6866; G01N 33/6878; G01N 2333/57; G01N 33/57515; G01N 33/505; C12Y 101/0103
See application file for complete search history.

(56) References Cited

U.S. PATENT DOCUMENTS

| | | | |
|---|---|---|---|
| 4,755,173 | A | 7/1988 | Konopka et al. |
| 4,957,108 | A | 9/1990 | Schoendorfer et al. |
| 5,080,653 | A | 1/1992 | Voss et al. |
| 5,097,122 | A | 3/1992 | Colman et al. |
| 5,190,863 | A | 3/1993 | Magers |
| 5,391,250 | A | 2/1995 | Cheney, II et al. |
| 5,485,408 | A | 1/1996 | Blomquist |
| 5,505,709 | A | 4/1996 | Funderburk et al. |
| 5,510,245 | A | 4/1996 | Magers |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,088,608 | A | 7/2000 | Schulman et al. |
| 6,119,028 | A | 9/2000 | Schulman et al. |
| 6,162,397 | A | 12/2000 | Jurik et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,485,465 | B2 | 11/2002 | Moberg et al. |
| 6,544,212 | B2 | 4/2003 | Galley et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,589,229 | B1 | 7/2003 | Connelly et al. |
| 6,591,876 | B2 | 7/2003 | Safabash |
| 6,641,533 | B2 | 11/2003 | Causey, III et al. |
| 6,659,980 | B2 | 12/2003 | Moberg et al. |
| 6,736,797 | B1 | 5/2004 | Larsen et al. |
| 6,740,072 | B2 | 5/2004 | Starkweather et al. |
| 6,749,587 | B2 | 6/2004 | Flaherty |
| 6,752,787 | B1 | 6/2004 | Causey, III et al. |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,817,990 | B2 | 11/2004 | Yap et al. |
| 6,827,702 | B2 | 12/2004 | Lebel et al. |
| 6,932,584 | B2 | 8/2005 | Gray et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,323,142 | B2 | 1/2008 | Pendo et al. |
| 7,399,277 | B2 | 7/2008 | Saidara et al. |
| 7,402,153 | B2 | 7/2008 | Steil et al. |
| 7,442,186 | B2 | 10/2008 | Blomquist |
| 7,602,310 | B2 | 10/2009 | Mann et al. |
| 7,621,893 | B2 | 11/2009 | Moberg et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Stoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 8,574,896 | B2 | 11/2013 | Nagakawa et al. |
| 9,987,427 | B1 | 6/2018 | Polsky et al. |
| 2004/0043376 | A1* | 3/2004 | Gupta ...................... C12Q 1/32 435/26 |
| 2004/0087671 | A1 | 5/2004 | Tamada et al. |
| 2005/0084921 | A1 | 4/2005 | Cranley et al. |
| 2007/0123819 | A1 | 5/2007 | Mernoe et al. |
| 2010/0045993 | A1 | 2/2010 | Martini et al. |
| 2010/0160861 | A1 | 6/2010 | Causey, III et al. |
| 2011/0105952 | A1* | 5/2011 | Bernstein ......... A61B 5/150755 600/573 |
| 2011/0118571 | A1 | 5/2011 | Mandelis et al. |
| 2011/0125058 | A1 | 5/2011 | Levinson et al. |
| 2017/0027482 | A1 | 2/2017 | Zilberstein et al. |
| 2017/0231571 | A1 | 8/2017 | Rogers et al. |
| 2018/0199866 | A1 | 7/2018 | Heikenfeld |
| 2018/0249935 | A1 | 9/2018 | Rao et al. |
| 2018/0303388 | A1 | 10/2018 | Rao et al. |
| 2020/0155047 | A1 | 5/2020 | Rogers et al. |

FOREIGN PATENT DOCUMENTS

| | | | |
|---|---|---|---|
| CN | 110573063 | A | 12/2019 |
| EA | 0140589 | A1 * | 9/1984 |
| EP | 0140589 | A1 | 5/1985 |
| EP | 0463524 | A1 | 1/1992 |
| WO | 0074763 | A2 | 12/2000 |
| WO | 2010/045247 | | 4/2010 |
| WO | 2010102294 | A1 | 9/2010 |
| WO | 2015102380 | A1 | 7/2015 |
| WO | 2016179559 | A2 | 11/2016 |
| WO | 2019126735 | A1 | 6/2019 |
| WO | 2020055791 | A1 | 3/2020 |

(56) References Cited

OTHER PUBLICATIONS

European Communication pursuant to Rule 164(2)(b) and Article 94(3) EPC dated Jun. 30, 2025 for EP Application No. 21783112.2.

Chinese Office Action dated Sep. 26, 2025 for Chinese Application No. 202180053819.2.

* cited by examiner

KETONE BODY SENSING DEVICE AND METHOD

CROSS-REFERENCE TO RELATED APPLICATIONS

This application claims the benefit of and priority to U.S. patent application Ser. Nos. 15/912,451 and 15/912,473, both of which were filed Mar. 5, 2018, and both of which claim the benefit of and priority to U.S. Provisional Patent Application Ser. No. 62/467,653, filed Mar. 6, 2017, the contents of which are incorporated herein by reference.

TECHNICAL FIELD

Embodiments of the subject matter described herein relate generally to medical devices, and more particularly, embodiments of the subject matter relate to the sensing of a ketone body in the interstitial fluid of a user for dietary or disease management.

BACKGROUND

Ketosis is a metabolic state in which some of the body's energy supply comes from ketone bodies in the blood. It can be identified by raised level of ketone bodies. Ketone bodies are water-soluble molecules produced from fatty acid oxidation in the liver and kidney during periods of low food intake (fasting), carbohydrate restrictive diets, starvation, prolonged intense exercise, alcoholism, or in untreated (or inadequately treated) type 1 diabetes. Acetoacetate, beta-hydroxybutyrate, and their decarboxylated degradation product, acetone, are the three primary ketone bodies. Other ketone bodies like β-ketopentanoate and β-hydroxypentanoate may be created as a result of the metabolism of synthetic triglycerides, such as triheptanoin. Beta-hydroxybutyrate is the reduced form of acetoacetate in which a ketone group is converted to an alcohol. Beta-hydroxybutyrate and acetoacetate can be used as an energy source when glucose stores are depleted.

High levels of ketone bodies can lead to ketosis. Ketosis is pathological in certain conditions, such as diabetes. Prolonged ketosis may lead to a life threatening metabolic acidosis. Specifically, in extreme type 1 diabetes, higher levels of ketone bodies leads to ketoacidosis. Pathological ketosis may indicate organ failure, hypoglycemia in children, diabetes, alcohol intoxication, corticosteroid or growth hormone insufficiency. Therefore, it is important for those with diabetes to know whether they are in ketosis or ketoacidosis.

Further, a number of clinical conditions can benefit from dietary ketosis, such as epilepsy and other neurological conditions, neurodegenerative diseases, and metabolic conditions. Ketosis can also be achieved purposely through a ketogenic diet or through prolonged or intermittent fasting.

The ketogenic diet is a low carbohydrate, high fat diet that was designed originally to manage seizures in children with epilepsy. The diet mimics the physiological state of fasting, which was known since the time of Hippocrates to reduce seizure susceptibility. An energy transition from carbohydrate metabolism to fat metabolism provides therapeutic benefits for disease management, such as for Type 2 diabetes, obesity, insulin resistance, and metabolic endocrine disorders.

Recently, the effects of a ketogenic diet, administered with drugs and hyperbaric oxygen therapy, has been found to help manage cancer. A similar therapeutic strategy could be used for managing neurological and neurodegenerative diseases.

Also, there is also a growing body of evidence that athletic performance can benefit from ketosis induced by diet, such as endurance enhancement. While the state of dietary ketosis is attainable, athletic benefit is greatest when the athlete remains in ketosis as prescribed, which can be difficult to sustain.

To be effective, the ketosis metabolic state must be maintained with care, as would be the case for any medical therapy. Improper diet could potentially produce hyperlipidemia and insulin insensitivity thereby reducing therapeutic benefit. Therefore, it is important for those seeking to remain in ketosis for therapeutic reasons to know whether they are in ketosis.

Heretofore, several methods for detecting ketosis have been used. First, invasive blood testing for the ketone body beta-hydroxybutyrate, such as performed by ketone blood strips and meters or by laboratory or medical offices has been used to identify the ketosis metabolic state. Second, testing of urine with ketone strips that detect the ketone body acetoacetate has been performed and is known to be somewhat effective, if time delayed, during the first few weeks of ketosis. However, the presence of acetoacetate in urine decreases over time in ketosis so urine testing may not be reliable. Third, there are devices that test the breath for acetone, a non-enzymatic metabolic byproduct of the ketone body acetoacetate. Such devices are typically expensive, require set up, and most importantly may lose accuracy when alcohol is present in the blood stream or when alcohol, breath mints, chewing gum, cough drops, throat lozenges, tobacco and e-cigarettes, lip balm, smoking, mint or green tea, mouthwash, non-sugar sweeteners, toothpaste, or water enhancers are on the breath.

Therefore, it would be beneficial to provide a convenient, inexpensive, and minimally invasive device and method for accurately detecting a ketone body, such as for determining whether a user is in ketosis or ketoacidosis. Such a device or method may be used for dietary and/or disease management. Further, it would be beneficial to provide a device and method for testing interstitial fluid for a ketone body. Also, it would be beneficial to provide a device and method that provides a visual indication of a threshold value of a ketone body in a sample.

BRIEF SUMMARY

Devices, patch sensors, and methods for detecting a ketone body are disclosed. An exemplary device includes a collection apparatus for collecting a sample of interstitial fluid and a ketone body indicator having an initial negative state and having a positive state when at least a threshold value of the ketone body is collected in the sample.

In another embodiment, a patch sensor is provided for detecting a ketone body. The patch sensor includes at least one hollow microneedle for penetrating skin of an individual to obtain interstitial fluid. Also, the patch sensor includes a collection indicator in fluid communication with the microneedle and having an initial state and a completed state when a sample amount of the interstitial fluid is collected. Further, the patch sensor includes a ketone body indicator having an initial negative state and having a positive state when at least a threshold value of the ketone body is collected in the sample amount.

In yet another embodiment, a method for detecting a metabolic state like ketosis or ketoacidosis in an individual is provided. The method includes adhering a ketone body sensor to skin of the individual. The ketone body sensor includes at least one hollow microneedle, a collection indicator in fluid communication with the microneedle and having an initial state and a completed state when a sample amount of the interstitial fluid is collected, and a ketone body indicator having an initial negative state and having a positive state when at least a threshold value of the ketone body is collected in the sample amount. The method also includes penetrating the skin of the individual with the microneedle, collecting interstitial fluid from the microneedle, and detecting a ketone body in the interstitial fluid with the ketone body sensor. Further, the method includes providing a visual indication with the collection indicator after the sample amount of the interstitial fluid is collected and observing the positive state of the ketone body indicator after the visual indication is provided.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
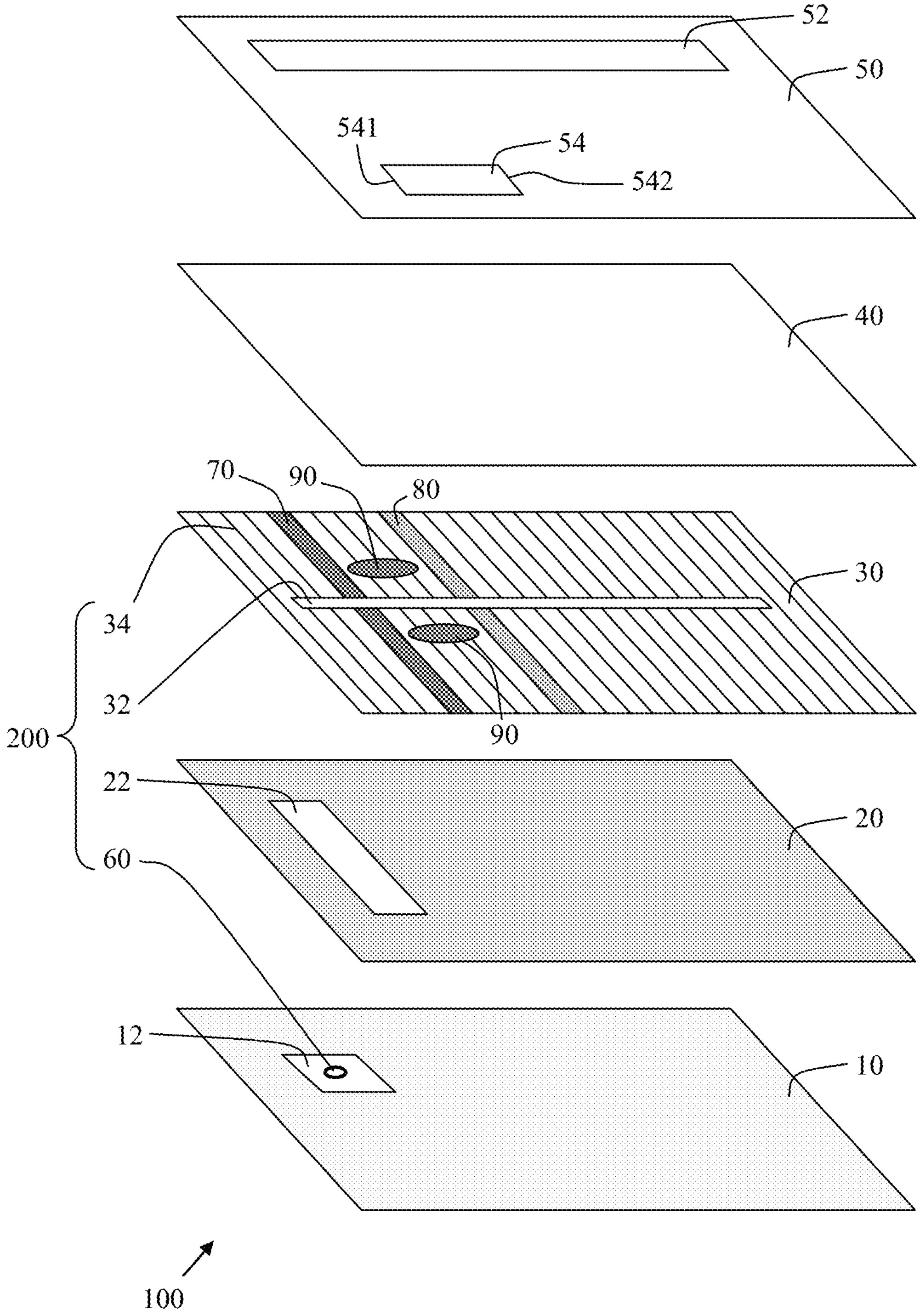
FIG. 1 is an expanded view of a device for detecting a ketone body showing various elements of device in accordance with one or more embodiments.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein may be implemented in a standalone fashion, such as for detection of at least one ketone body in an individual's interstitial fluid (e.g., detect a level of ketone bodies) to provide metabolic state awareness, i.e., determine if the individual is in ketosis or in ketoacidosis, by an inexpensive, disposable, single-use device. In an exemplary embodiment, the device uses a colorimetric agent to provide a simple-to-read indication that the individual is or is not in the metabolic state (ketosis or ketoacidosis), or that the individual's interstitial fluid includes at least a threshold value of a selected ketone body (e.g., detect a level of ketone bodies). In certain embodiments, the simple-to-read indication may be a change in optical properties, such as a change from clear or transparent to a selected color that is easily distinguished by the individual's eyesight. A chart providing examples of color intensity associated with predetermined levels of the ketone body may be provided on or with the device to facilitate interpretation of the optical change, e.g., final indicator color. In other embodiments, the simple-to-read indication may be a change in optical properties, such as a change from clear or transparent to a selected color that is easily distinguished by a computing device, such as a smart phone that captures an image of the optical change. The computing device may be provided with or have access to an electronic library or chart providing examples of color intensity associated with predetermined levels of the ketone body.

While the device described herein may be used to detect any desired ketone body in interstitial fluid, in exemplary embodiments, the sensor detects beta-hydroxybutyrate (BHB), also known as β-hydroxybutyrate (β-HB) or as 3-hydroxybutyrate. During ketosis, beta hydroxybutyrate increases more than the other ketone bodies and may be a more accurate index of ketoacidosis. Beta-hydroxybutyrate may form about 70% of total ketone bodies produced via oxidation of free fatty acids.

Certain embodiments of the device may be provided in conjunction with a glucose sensor. Specifically, a ketone body sensor and a glucose sensor may be provided in or on a single device. Such an embodiment may be of particular need by individuals with diabetes. Examples of a glucose sensor may be of the type described in, but not limited to, United States Patent Appl. Nos.: 2018/0249935 and 2018/0303388, each of which are herein incorporated by reference.

Still other embodiments described herein may be utilized in conjunction with medical devices, such as portable electronic medical devices. Although many different applications are possible, exemplary embodiments are used in applications that incorporate a fluid infusion device (or infusion pump) as part of an infusion system deployment. That said, the subject matter described herein is not limited to use with infusion devices (or any particular configuration or realization thereof) or with a multiple daily injection (MDI) therapy regimen or with other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) are not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Referring now to FIG. 1, an expanded view of a device 100, such as a patch sensor 100, for detecting a ketone body (e.g., detecting a level of ketone bodies) is provided. As described, the device 100 is a colorimetric ketone screening patch that can identify a normal level or therapeutic level of ketosis or identify ketoacidosis.

As shown, the device 100 is in the form of a stack of layers, including an adhesive layer 10, a collection layer 20 over the adhesive layer 10, a sensor layer 30 over the collection layer 20, an intermediate layer 40 over the sensor layer 30, and a cover layer 50 over the intermediate layer 40. As further shown, the device 100 includes at least one hollow microneedle 60. Further, the device 100 includes a ketone body indicator 70, a collection indicator 80, and optional additional sensors or indicators 90, such as a glucose sensor and/or pH sensor, or other desired sensors/indicators for evaluating interstitial fluid.

Microneedle

In an exemplary embodiment, the at least one hollow microneedle 60 (e.g., one, two, three, ten or any other number of hollow microneedles) is provided for penetrating the skin of an individual. Specifically, the microneedle 60 is configured to pierce the individual's skin to a depth sufficient to collect interstitial fluid, such as into a subdermal region of the skin. For example, the microneedle 60 may be provided to extend into the skin at a depth of from about 0.3 to about 2 millimeters (mm), such as about 1 mm. An exemplary microneedle 60 is formed as a micro-molded plastic hollow microneedle, or as a silicon hollow microneedle. The microneedle 60 may be formed from other suitable materials.

Further, in an exemplary embodiment, the at least one hollow microneedle 60 includes an array of microneedles 60. The number of microneedles 60 may be selected so that sufficient amount of interstitial fluid is collected in a desired time period. For example, one microneedle 60 may collect about two to about three microliters (μL) in about one half hour. Therefore, the device 100 may include about one to about ten microneedles to collect a sufficient amount of interstitial fluid in from about three to about five minutes. Of course, other numbers or types of microneedles may be used as desired to provide for sufficient collection of interstitial fluid over any desired time period. For example, in some embodiments, the device 100 may be designed to accumulate a sample volume of interstitial fluid and provide sufficient time for chemical reaction in the device 100 to complete the detection test in fifteen to twenty minutes.

Adhesive Layer

In an exemplary embodiment, the adhesive layer 10 includes an adhesive that is adapted to bond to the skin of an individual. The adhesive layer 10 further includes a film on which the adhesive is applied. The adhesive layer 10 may be formed from adhesive patches and patch transfer tape, for example Papilio (Color Laser Clear Glossy Polyester Film), or printable polyester sheets used to laminate layers and create constructs. These sheets can be printable and have adhesive on one side. The adhesive layer 10 may be formed from other suitable materials. While not shown, the adhesive layer 10 may be provided on a backing sheet or substrate, such that the adhesive is located between the backing sheet and the film until ready for use.

As shown, the adhesive layer 10 may be formed with a gap 12 surrounding the microneedle 60. In the gap 12 of the adhesive layer 10, no adhesive is located on the film. As may be understood, the microneedle 60 passes through the film of the adhesive layer 10 to define a fluid path through the adhesive layer 10.

Collection Layer

In an exemplary embodiment, the collection layer 20 is formed directly on the adhesive layer 10. More specifically, the collection layer 20 may be formed directly on the film of the adhesive layer 10. The collection layer 20 may be a layer of any suitable material. For example, the collection layer may be formed from plastics, e.g., polyvinyl chloride (PVC), high-density polyethylene (HDPE), low-density polyethylene (LDPE), polyethylene terephthalate (PET), polypropylene, or the like, a fabric (woven or non-woven), paper, filter paper, nitrocellulose, cellulose, polyester, and/or other suitable materials. An exemplary collection layer 20 may be formed with as a white color to provide a white background to facilitate observation of a colorimetric agent optical change, as described below. An exemplary collection layer 20 includes a collection port 22 in fluid communication with the microneedle 60. As a result, interstitial fluid may flow from the individual and through the microneedle 60, and be collected in the collection port 22. The collection port 22 is partially encapsulated by the film of the adhesive layer 10 and by sidewalls of the collection layer 20.

Sensor Layer

In an exemplary embodiment, the sensor layer 30 is formed directly on the collection layer 20. As shown, the exemplary sensor layer 30 is formed with a void or feed channel 32 that runs in a longitudinal direction of the device 100. The feed channel 32 is in fluid communication with the collection port 22 of the collection layer 20 such that interstitial fluid may flow from the collection port 22 into the feed channel 32. In this manner, the sensor layer 30 accumulates interstitial fluid that migrates through the microneedle 60.

An exemplary sensor layer 30 may be a substrate formed from plastics, a fabric (woven or non-woven), paper, filter paper, nitrocellulose, cellulose, polyester, porous hydrogels, materials which can be wax printed to create hydrophobic regions, and/or other suitable materials.

Therefore, the sensor layer 30 may be formed with microfluidic technology 34 in fluid communication with the feed channel 32. For example, the microfluidic technology 34 may be embodied by fluidic capillary channels that extend transverse to the feed channel 32. For example, the fluidic capillary channels may be formed on the surface of the sensor layer 30 and may extend in a lateral direction of the device 100, perpendicular to the feed channel 32. Because the fluidic capillary channels are in fluid communication with the feed channel 32, interstitial fluid may be drawn along the fluidic capillary channels of the microfluidic technology 34 outward from the feed channel 32 by the capillary forces.

In certain embodiments, the microfluidic technology 34 may include treatment or modification of the sensor layer 30 to selectively encourage or inhibit fluid flow. For example, the sensor layer 30 may be at least partially modified to change its hydrophobic or hydrophilic nature. An exemplary sensor layer 30 may be formed from a porous hydrophilic or hydrophobic substrate and be treated with a hydrophobic or hydrophilic coating, respectively. In an exemplary embodiment, the sensor layer includes a hydrophilic coating applied to at least a portion of a substrate fabricated from a hydrophobic material such as polydimethylsiloxane (PDMS). Hydrophilic materials that may be used include, but are not limited to, 2-hydroxethyl methacrylate (HEMA), poly(oxyethylene) (POE), silicon dioxide, poly(ethylene glycol) (PEG), and polyacrylamide. Surface modifications of PDMS may also be performed by, for example, oxygen plasma treatments and/or UV-mediated grafting.

Hydrophobic and hydrophilic barriers can be created by other methods such as by spraying hydrophobic polymers (e.g. polydimethylsiloxane) on the substrate using a mask to cover the required hydrophilic regions. Hydrophobic and hydrophilic barriers can be created by printing wax with a wax printer, by paraffin stamped on paper, through the use of hydrogels (e.g., silica gels on hydrophobic base material). Generally, hydrophobic and hydrophilic materials can be used to modify sensor elements and create hydrophobic pathways that direct the flow of interstitial fluid through the sensor (e.g., APTES surface modified on transparency sheets to create pathways). In this context, WO2010102294A1 discloses illustrative methods for doing so to create micropatterning paper based microfluidics (e.g. printing of a solid wax ink onto a paper substrate in a predetermined pattern defining an assay region to allow for the manufacture of microfluidic analytical sensor). The hydrophobic regions may be created in this manner (but are not required if sensor is designed according to other embodiments).

Additionally, one or more features may be added to the sensor layer 30 using conventional techniques. As discussed above, these features may include channels, reaction zones, spacers, or transparent layers. Also, features may be formed in the sensor layer 30, such as buffers, analytes or enzyme coatings, as well visual indicators to facilitate the user interface (e.g. indicators of ketone body concentrations, test completion, glucose levels or pH) or the like.

As a result, in certain embodiments, the sensor layer 30 includes hydrophilic regions and hydrophobic regions adapted to modulate the flow of interstitial fluid through the device. This creates a fluidic path that directs interstitial fluid to a reaction zone, i.e., at the ketone body indicator and, optionally, at the collection indicator and other indicators if provided. Thus, a fluidic flow is created with a positive flow from an interstitial fluid collection port, i.e., the microneedle 60, to the reaction zone.

Collectively, the microneedle 60, collection port 22, feed channel 32, and microfluidic technology 34 form a collection apparatus 200 for collecting a sample of interstitial fluid. The collection apparatus 200 includes the fluidic path directing interstitial fluid from the microneedle 60 to the ketone body indicator 70.

Ketone Body Indicator

As shown in FIG. 1, the ketone body indicator 70 is formed on and/or in the sensor layer 30. As a result, a capillary flow path connects the collection apparatus 200 to the ketone body indicator 70.

An exemplary ketone body indicator 70 has an initial negative state and has a positive state when at least a threshold value of the ketone body is collected in the sample amount. In other words, such as ketone body indicator 70 is configured to change to the positive state when at least a threshold value of the ketone body is collected in the sample amount. In an exemplary embodiment, the ketone body is beta-hydroxybutyrate.

In an exemplary embodiment, the ketone body indicator is formed as a colorimetric system. Such a ketone body indicator may include an enzyme that catalyzes a reaction of the ketone body, an enzyme cofactor, and a colorimetric agent exhibiting an initial optical property and configured to change to a second optical property when the threshold value of the ketone body is collected in the sample amount. More specifically, the exemplary ketone body indicator includes an enzyme that catalyzes a reaction of the ketone body, an enzyme cofactor that is reduced to a reduced cofactor form during the reaction of the ketone body, an electron mediator, and a colorimetric agent that is reduced to a visible compound during oxidation of the reduced cofactor form in the presence of the electron mediator. In certain embodiments, the enzyme is 3-hydroxybutyrate dehydrogenase, the enzyme cofactor is nicotinamide adenine dinucleotide (NAD+), the electron mediator is selected from mPMS (1-Methoxy-5-methylphenazinium), potassium ferricyanide, and 1,10, phenanthroline, and the colorimetric agent is a water soluble tetrazolium (WST), though other suitable compounds may be used. For example, other colorimetric agents that may be useful include Trinder reagents, MTT, MTS, as well as resazurin (reduced product of resazurin fluoresces to green light).

Water-soluble tetrazolium salts are a series of water-soluble dyes that are reduced in the presence of electron mediators to water-soluble formazan dyes exhibiting different absorption spectra. A tetrazolium salt may be selected based on the absorption spectrum of the associated formazan dye. Exemplary water soluble tetrazoliums include WST4 (2-Benzothiazolyl-3-(4-carboxy-2-methoxyphenyl)-5-[4-(2-sulfoethyl carbamoyl) phenyl]-2H-tetrazolium), WST5 (2,2'-Dibenzothiazolyl-5,5'-bis[4-di(2-sulfoethyl) carbamoylphenyl]-3,3'-(3,3'-dimethoxy 4,4'-biphenylene) ditetrazolium, disodium salt), and WST8 (2-(2-methoxy-4-nitrophenyl)-3-(4-nitrophenyl)-5-(2,4-disulfophenyl)-2H-tetrazolium, monosodium salt), though other water soluble tetrazoliums may be used.

In certain embodiments, the ketone body indicator 70 further includes a co-enzyme and an enzyme stabilizer. An exemplary co-enzyme is diaphorase, though other suitable co-enzymes may be used. An exemplary enzyme stabilizer is trehalose, though other suitable enzyme stabilizers may be used.

In certain embodiments, the ketone body indicator 70 and/or the colorimetric agent is coupled to the sensor layer 30. For example, in some embodiments, the ketone body indicator 70 and/or the colorimetric agent is immobilized using a poly(vinyl alcohol) (PVA) substituted with styrylpyridinium (SbQ), and/or a chitosan and/or a polyethyleneimine.

Collection Indicator

As further shown in FIG. 1, the collection indicator 80 is formed on and/or in the sensor layer 30. An exemplary collection indicator 80 has an initial state. Further, the exemplary collection indicator 80 has a completed state when contacted by a sufficient amount of the interstitial fluid for the ketone body sensor to effectively detect the ketone body (e.g., detect a level of ketone bodies).

In an exemplary embodiment, the collection indicator 80 is a hydrochromic ink which changes from being transparent to being colored, or from being colored to being transparent, upon being wetted. Alternatively, the collection indicator 80 may use a colorimetric system similar to the ketone body indicator, but adapted to change optical property upon contact with a different compound or at a different concentration of compound. The collection indicator may be formed as described above in relation to the ketone body indicator. In an exemplary embodiment, the collection indicator may be a system including cobalt chloride, chlorophenol red, test paper commercially available as Hydrion® Water Finder Tester from Micro Essential Laboratory of Brooklyn, N.Y., and/or indicator tape commercially available as 3M™ Water Contact Indicator Tape from 3M Company of St. Paul, Minn.

In an exemplary embodiment, the ketone body indicator 70 is located between the collection port 22 in the collection layer 20 and the collection indicator 80. As a result, the ketone body indicator 70 is contacted by the interstitial fluid before the collection indicator 80 is.

Additional Indicators

In certain embodiments, additional sensors or indicators 90 may be formed on and/or in the sensor layer 30.

For example, a glucose sensor may be formed on and/or in the sensor layer 30 for detecting glucose in the interstitial fluid. An exemplary glucose sensor may include an enzyme complex that reacts with glucose and comprises: glucose oxidase, glucose dehydrogenase or a hexokinase/glucose-6-phosphate complex and a colorimetric agent that changes color following reaction of glucose with the enzyme complex. Optionally in these embodiments, the colorimetric indicator in the glucose sensing complex is clear or is a first color when the concentration of glucose in the interstitial fluid of the individual is less than a first level (e.g., 1.8 mg/dL), and a second color when the concentration of glucose is greater than the first level (e.g., greater than 1.8 mg/dL). Further, for such embodiments, a color indicator (e.g., a color chart/key) that shows an optical property such as a color (or transparency) of the glucose sensor when the concentration of glucose is greater than 1.8 mg/dL.

Further, a pH sensor may be formed on and/or in the sensor layer 30 for indicating the pH of the interstitial fluid. The pH of interstitial fluid can vary (e.g., from about 3.5 to about 7.5), while certain ketone body sensing complexes are effective in the range of pH of from about 7.5 to about 9. An optimized interstitial fluid pH in embodiments herein can be achieved by adjusting the pH such as by using pre-dried buffers (such as TRIS, PBS, HEPES and the like) on the sensor layer or other layers, or by alternatively using ion exchange materials coated on the sensor layer or other layers. Consequently, in certain embodiments, a region of the substrate layer in which the ketone body sensing complex is disposed includes preloaded buffering compounds adapted to modulate the pH at which the ketone body sensing complex senses the ketone body. Other embodiments may include an anion exchange paper (e.g., DE81, GE) to convert the interstitial fluid to hydroxide anions which help buffer the interstitial fluid to a pH of from about 7 to about 9. Such embodiments can include a pH sensor like pH paper or the like to indicate if pH of the interstitial fluid sample is optimal.

Intermediate Layer

As shown in FIG. 1, the intermediate layer 40 is formed directly on the sensor layer 30. In the illustrated embodiment, the exemplary intermediate layer 40 encapsulates the feed channel 32 and the microfluidic technology 34. As a result, the fluid flow path from the microneedle 60 into the interior of the device 100 terminates at the intermediate layer 40.

An exemplary intermediate layer 40 is a transparent adhesive film. For example, the intermediate layer 40 may be formed from plastics, e.g., polyester, cellulose, polypropylene, and/or cellophane) a fabric (woven or non-woven), paper, filter paper, nitrocellulose, cellulose, polyester, and/or other suitable materials. An exemplary intermediate layer 40 is formed from material selected to minimize evaporation of the interstitial fluid that is being transported in the channels underlying the intermediate layer 40.

Cover Layer

As shown in FIG. 1, the cover layer 50 is formed directly on the intermediate layer 40. The exemplary cover layer 50 is opaque and includes a transparent viewing window 52. As a result, the ketone body indicator 70, collection indicator 80, and other indicators 90, may be viewed by the individual through the transparent window 52. While a single window 52 is shown in the embodiment of FIG. 1, it is envisioned that multiple windows may be provided in order to allow viewing of each indicator 70, 80, and 90.

An exemplary cover layer 50 is opaque and may be formed from plastics, e.g., polyvinyl chloride (PVC), high-density polyethylene (HDPE), low-density polyethylene (LDPE), polyethylene terephthalate (PET), polypropylene, or the like, a fabric (woven or non-woven), paper, filter paper, nitrocellulose, cellulose, polyester, and/or other suitable materials. An exemplary transparent window 52 may be formed by any suitable materials. For example, the transparent window 52 may be polyester, cellulose, polypropylene, cellophane, and/or a film commercially available as Tegaderm from 3M Company of St. Paul, Minn.

As shown, the cover layer 50 may be provided with a color comparison chart 54. Such a chart 54 may allow an individual to visually compare the ketone body indicator 70 with the chart 54 to identify the ketone body level measured by the ketone body indicator 70. Though not illustrated in FIG. 1, an exemplary color chart 54 includes a plurality of color sections or swatches having differing optical densities, such as increasing optical densities from a first end 541 to a second end 542. For example, at a first end 541, the color chart 54 may include a color section with a low optical density correlating to a ketone body level of zero or near zero. At a second end 542, the color chart 54 may include a color section with a high optical density correlating to a high level of ketone bodies. Gradients of optical densities are provided for color sections between the first end 541 and the second end 542 so that various levels of ketone bodies may be visually identified. In an exemplary embodiment detecting beta-hydroxybutyrate, the color section at the first end 541 of the color chart 54 may have an optical density correlated to ketone body levels of 0 millimoles per liter (mmol/L) or millimolar (mM). In an exemplary embodiment, the color section at the second end 542 of the color chart 54 may have an optical density correlated to a selected ketone body level, such as 2.0 mmol/L, 3.0 mmol/L, 4.0 mmol/L, or other desired ketone body level. An exemplary color chart 54 may include intermediate sections between the first end 541 and second end 542 that have optical densities correlated to increasing ketone body levels, such as 0.5, 1.0, 1.5, 2.0, 2.5, 3.0, and 3.5 mmol/L. The increments between sections of the color chart 54 may be provided with any desired increase in ketone body levels. In other words, the color chart may provide any suitable range of color gradients for use in the device 100.

The specific colors of the color comparison chart may be selected based on the colorimetric agent used. Specifically, the colors will be dependent on choice of the colorimetric agent as the colorimetric agents have different operating absorbance windows. For example, for the colorimetric agent WST-8, the spectrum of the by-product is a strong orange dye with a maximum adsorption at 450 nm. Thus, an exemplary color comparison chart 54 would include gradients from no color, through pale yellow, to dark orange. Certain other WST colorimetric agents, such as WST-5, provide a pale green to dark green spectrum.

Figure 2:
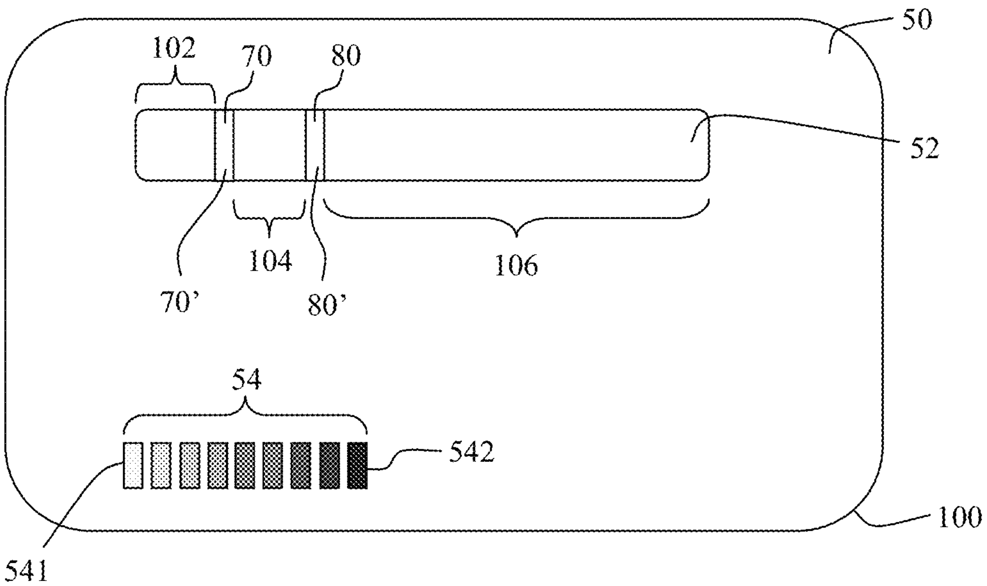
FIG. 2 is a top view of the device of FIG. 1 with the ketone body indicator in an initial negative state and the collection indicator in an initial state.
Figure 3:
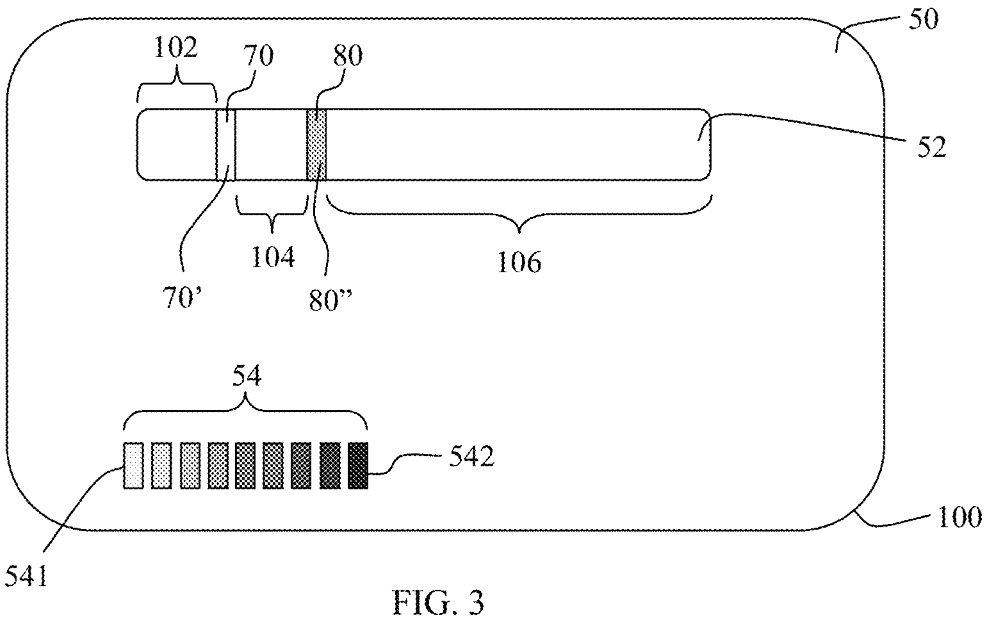
FIG. 3 is a top view of the device of FIG. 1 with the ketone body indicator remaining in the negative state and the collection indicator in a completed state.
Figure 4:
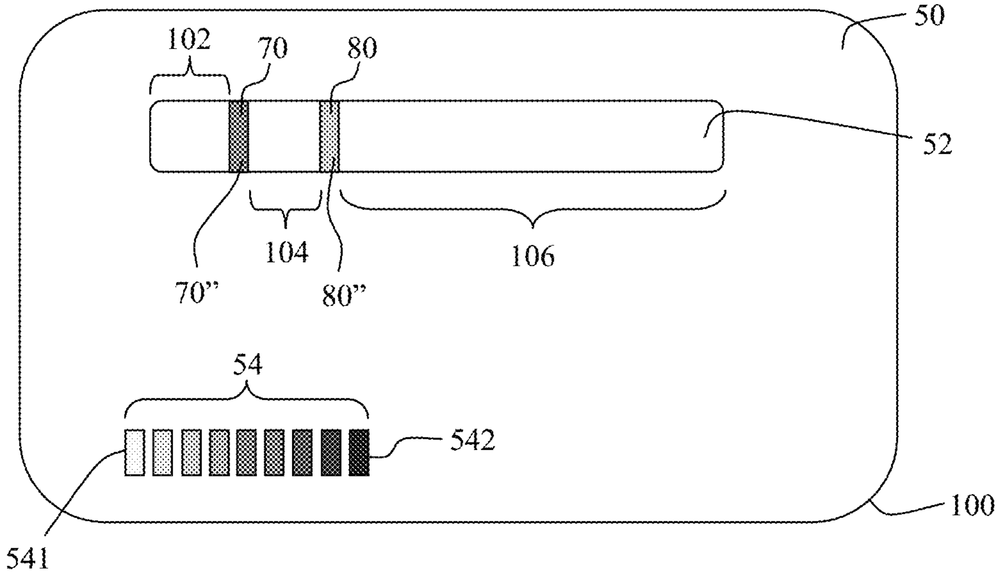
FIG. 4 is a top view of the device of FIG. 1 with the ketone body indicator in a positive state and the collection indicator in a completed state.

Cross-referencing FIGS. 2-4, operation of the device 100 may be further understood. FIGS. 2-4 are top views of the device 100, i.e., the cover layer 50 is facing the viewer, with internal components viewable through the window 52 and the color chart provided on the cover 50.

Referring to FIG. 2, the device 100 of FIG. 1 is shown with the ketone body indicator 70 in an initial negative state 70' and the collection indicator 80 in an initial state 80'. The device 100 is in this initial condition after being manufactured, during shipping, and before use. In the embodiment illustrated, the ketone body indicator 70 and the collection indicator 80 are both clear or transparent when in the initial states 70' and 80'.

Referring to FIG. 3, the device 100 of FIG. 1 is shown with the ketone body indicator 70 remaining in the negative state 70' and with the collection indicator 80 in a completed state 80". The device 100 is in this condition after the sample amount of interfacial fluid is collected by the device 100 and the sample amount of interfacial fluid includes less than the threshold value of the ketone body. In the embodiment illustrated, the ketone body indicator 70 remains clear or transparent when in the negative state 70' and the collection indicator 80 is colored in the completed state 80". However, in other embodiments, the ketone body indicator 70 exhibits an optical change such as a color change, though to a lighter color than a predetermined color indicative of the threshold value of the ketone body.

Referring to FIG. 4, the device 100 of FIG. 1 is shown with the ketone body indicator 70 remaining in the positive state 70" and with the collection indicator 80 in the completed state 80". The device 100 is in this condition after the sample amount of interfacial fluid is collected by the device 100 and the sample amount of interfacial fluid includes at least the threshold value of the ketone body. In the embodiment illustrated, the ketone body indicator 70 is colored in the positive state 70" and the collection indicator 80 is colored in the completed state 80". Specifically, in the positive state 70", the ketone body indicator 70 has an optical density equal or greater than a predetermined value. In certain embodiments, the device 100 may be designed such that the color of the ketone body indicator 70 in the positive state 70" is the same as the color of the collection indicator 80 in the completed state 80".

In the embodiment of FIGS. 2-4, the ketone body indicator 70 and the collection indicator 80 are parallel and distanced from one another by a preselected distance such that the collection indicator 80 automatically changes color, i.e., provides an alert, when the ketone body indicator 70 is sufficiently contacted by the sample amount of interstitial fluid. Specifically, it may be seen that the device 100 has an initial time period for accumulating interstitial fluid indicated by reference number 102. The initial time period 102 commences with the placement of the microneedle 60 in the subdermal region of the skin and continues until the interstitial fluid reaches the ketone body indicator 70.

As further shown, the device 100 effectively provides a “wait time” indicated by reference number 104, wherein the amount of interstitial fluid in contact with the ketone body indicator 70 increases as the interstitial fluid flows into the device under capillary flow forces until the amount of interstitial fluid in contact with the ketone body indicator 70 reaches the sample amount. In exemplary embodiments, the sample amount is from about 5 to about 25 microliters (μL), such as from about 5 to about 10 μL, though other sample amounts may be used. The device 100 determines that the sample amount of interstitial fluid has contacted the ketone body indicator 70 with the collection indicator 80. Specifically, the collection indicator 80 changes from the initial state 80' to the completed state 80" when contacted by a predetermined amount of interstitial fluid indicative that the sample amount of interstitial fluid has contacted the ketone body indicator 70.

Therefore, the visual indication provided by the change of the collection indicator 80 to the completed state 80" provides a “read now” message to the user that the device 100 may be read for a result by the ketone body indicator 70 because the sample amount of the interstitial fluid has been collected. The region indicated by reference number 106 may be considered to be indicative of the accumulation of excess interstitial fluid.

Figure 5:
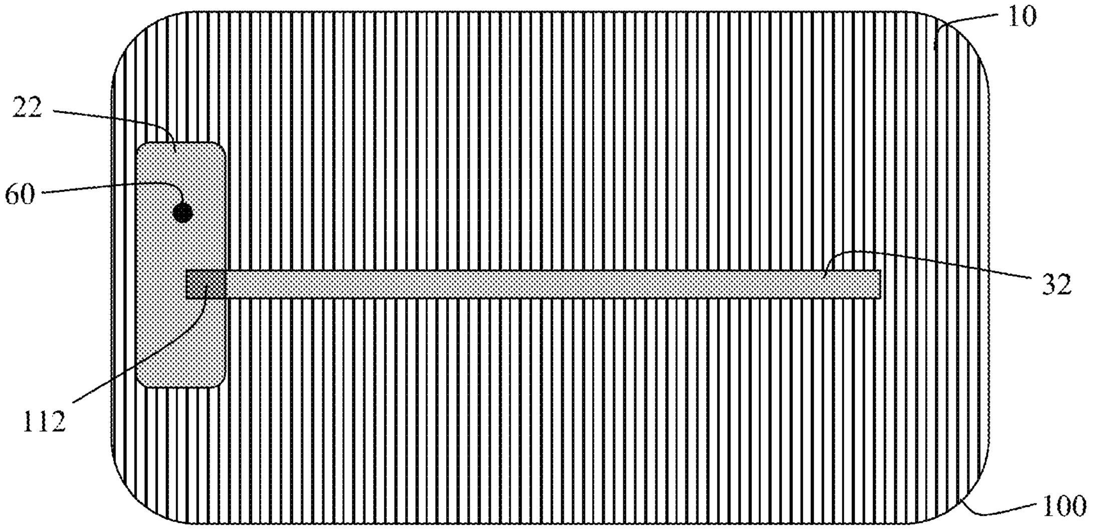
FIG. 5 is a bottom view of the device of FIG. 1.

Referring now to FIG. 5, the structure of the device 100 may be further understood. FIG. 5 is a bottom view of the device 100, i.e., the adhesive layer 10 is facing the viewer. It is noted that the layers 10, 20, 30 and 40 are at least partially transparent such that internal components of the device 100 are visible through the adhesive layer 10. As shown, the collection port 22 lies directly over the microneedle 60. Further, a portion of the feed channel 32 in the sensor layer lies directly over the collection port 22 in the collection layer. Thus, a direct flow path 112 connects the collection port 22 and the feed channel 32.

Figure 6:
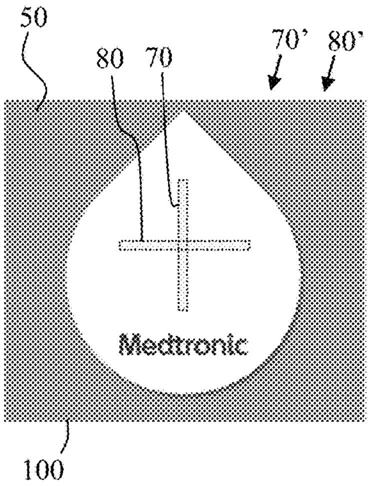
FIG. 6 is a front view of another exemplary embodiment of the device of FIG. 1 with the ketone body indicator in an initial negative state and the collection indicator in an initial state.
Figure 7:
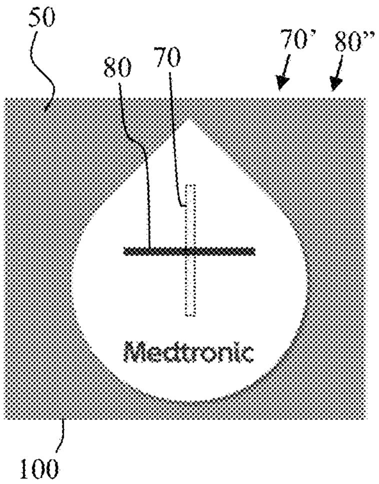
FIG. 7 is a front view of the device of FIG. 6 with the ketone body indicator remaining in the negative state and the collection indicator in a completed state.
Figure 8:
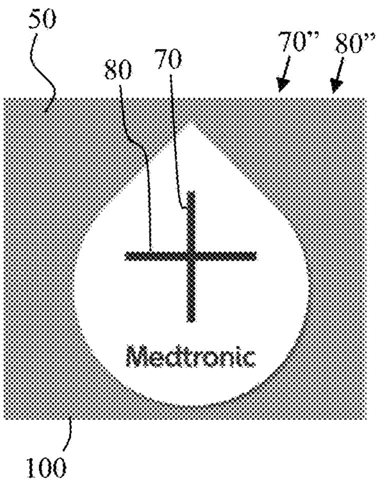
FIG. 8 is a front view of the device of FIG. 6 with the ketone body indicator in a positive state and the collection indicator in a completed state.

Cross-referencing FIGS. 6-8, operation of another embodiment of device 100 may be understood. FIGS. 6-8 are top views of the device 100, i.e., the cover layer 50 is facing the viewer, with internal components viewable through the window 52.

Referring to FIG. 6, the device 100 is shown with the ketone body indicator 70 in the initial negative state 70' and the collection indicator 80 in the initial state 80'. The device 100 is in this initial condition after being manufactured, during shipping, and before use. As with the previously described embodiment, the ketone body indicator 70 and the collection indicator 80 may both be clear or transparent when in the initial states 70' and 80'.

Referring to FIG. 7, the device 100 of FIG. 6 is shown with the ketone body indicator 70 remaining in the negative state 70' and with the collection indicator 80 in a completed state 80". The device 100 is in this condition after the sample amount of interfacial fluid is collected by the device 100 and the sample amount of interfacial fluid includes less than the threshold value of the ketone body. As with the previously illustrated embodiment, the ketone body indicator 70 remains clear or transparent when in the negative state 70' and the collection indicator 80 is colored in the completed state 80". Of course, the ketone body indicator 70 may exhibit a color change, though not to the color of the positive state 70", when in the negative state 70'.

Referring to FIG. 8, the device 100 of FIGS. 6 and 7 is shown with the ketone body indicator 70 remaining in the positive state 70" and with the collection indicator 80 in the completed state 80". The device 100 is in this condition after the sample amount of interfacial fluid is collected by the device 100 and the sample amount of interfacial fluid includes at least the threshold value of the ketone body. As with the previously described embodiment, the ketone body indicator 70 is colored in the positive state 70" and the collection indicator 80 is colored in the completed state 80".

In the embodiment of FIGS. 6-8, the ketone body indicator 70 and the collection indicator 80 are transverse to one another, specifically perpendicular to one another. As a result, the device 100 displays a “minus” sign when the test is completed (e.g., as shown in FIG. 7), i.e., when the sample amount of interstitial fluid is collected, and the level of ketone body in the interstitial fluid is less than the threshold value. Further, the device 100 displays a "plus" sign when the test is completed (e.g., as shown in FIG. 8), i.e., when the sample amount of interstitial fluid is collected, and the level of ketone body in the interstitial fluid is equal to or greater than the threshold value. While not illustrated, the embodiment of FIGS. 6-8 may include a color chart on the cover 50.

Figure 9:
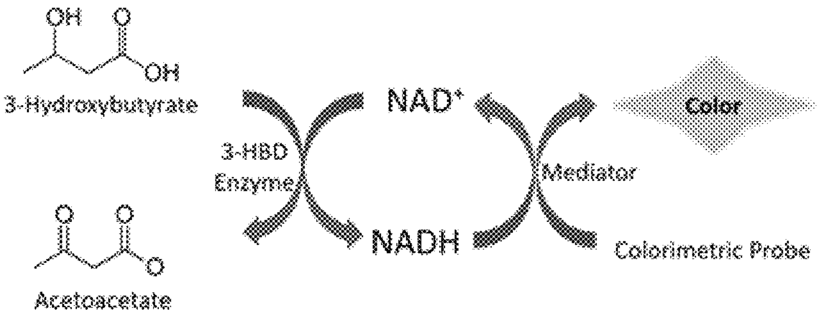
FIG. 9 is a schematic of a ketone body detection scheme in accordance with one or more embodiments.

FIG. 9 illustrates an exemplary ketone body detection scheme for use by the device 100 according to embodiments of FIGS. 1-8.

In FIG. 9, the sensor may detect a level of ketone bodies, for example detect a selected ketone body, such as beta-hydroxybutyrate, through use of the illustrated enzymatic cycling reaction in which the cofactor NAD+, i.e., the oxidized form of nicotinamide adenine dinucleotide (NAD), is reduced to NADH, i.e., the reduced form of NAD. Specifically, beta-hydroxybutyrate is converted into acetoacetate in the presence of the enzyme, beta-hydroxybutyrate dehydrogenase (β-hydroxybutyrate dehydrogenase or BDH1) while the enzyme cofactor, NAD+, is reduced to NADH.

As further shown, the NADH then is oxidized to NAD+ through a reaction with a colorimetric agent or probe that produces a product color, in the presence of an electron mediator. An exemplary colorimetric agent is a water soluble tetrazolium (WST) that is reduced in the presence of the electron mediator to a water-soluble formazan dye exhibiting a selected absorption spectrum. The intensity of the product color is proportional to the beta-hydroxybutyrate within the sample amount of interstitial fluid. In FIG. 9, the product color has an optical density (OD) of 450 nanometers (nm). As is easily understood, the components for performing the ketone body detection scheme may be selected to provide the product color with a desired optical density when the threshold value of the ketone body is detected in the sample amount of interstitial fluid.

The color or optical density of a product color may be evaluated on its own to ascertain the amount of the ketone body in the sample amount. Alternatively, the color or optical density of the product color may be compared to the colors or optical densities of pre-evaluated levels of the ketone body.

In various embodiments of the device 100, the threshold value of the ketone body is preselected to provide an indication of ketosis, ketoacidosis, or other condition as desired. For example, in an exemplary embodiment, the threshold value of the ketone body is one millimole per liter (mmol/L) in the sample amount of interstitial fluid. While any threshold value may be selected, other threshold values may be 0.5, 0.75, 1.25, 1.5, 1.75, 2.0, 2.25, 2.5, 2.75, 3.0 mmol/L, or any other value of ketone body in the interstitial fluid.

For beta-hydroxybutyrate, a ketone body level of less than 0.5 mmol/L is not considered ketosis. Beta-hydroxybutyrate levels of from 0.5 to 3.0 mmol/L are typically indicative of nutritional ketosis. For some, beta-hydroxybutyrate levels of from 1.5 to 3.0 mmol/L provide optimal ketosis.

When managing diabetes, a beta-hydroxybutyrate level of less than 0.5 mmol/L is generally safe. A beta-hydroxybutyrate level of from 0.5 to 1, 1 to 1.5, or 1.5 to 2.0 mmol/L may require some individuals to take additional insulin over the otherwise indicated insulin dose. For most individuals, a beta-hydroxybutyrate level of 2.0 mmol/L or greater may require additional insulin over the otherwise indicated insulin dose. For most individuals, a beta-hydroxybutyrate level of 3.0 mmol/L or greater may require immediate medical review. Thus, in embodiments herein, a device 100 may be designed with a first threshold value for use in identifying ketosis and a second threshold value for use in identifying ketoacidosis.

In various embodiments of the device 100, the sample amount of interstitial fluid is from five to twenty-five microliters (μL). However, any sample amount of interstitial fluid sufficient to allow for the detection of the ketone body by the device may be used. For example, the sample amount may be five to thirty, five to forty, five to fifty microliters, or other suitable amount.

Figure 10:
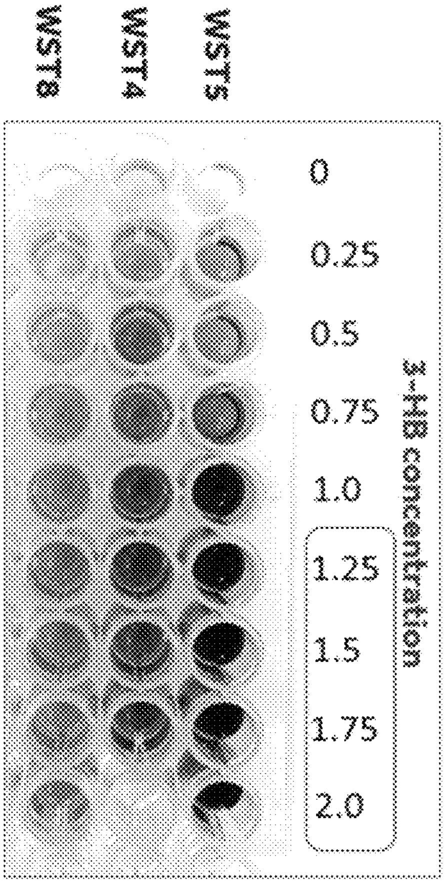
FIG. 10 is a photograph of data generated in a study of ketone body detection using a ketone body indicator as described in one or more embodiments.

Now referring to FIG. 10, a photograph of data generated in a study of ketone body detection using an exemplary ketone body indicator is provided. FIG. 10 shows the test results for ketone body indicators using three different colorimetric agents (WST8, WST4, and WST5) at various concentrations of beta-hydroxybutyrate (3-HB). As shown for each ketone body indicator, an initial optical property, e.g., transparency, is maintained and results when the tested sample amount of interstitial fluid has a beta-hydroxybutyrate concentration of 0 mmol/L. At 0.25 mmol/L, each ketone body indicator has a changed optical property, i.e., a color change. Continued color change exists for each ketone body indicator at the progression of beta-hydroxybutyrate concentrations. Thus, in practice the colorimetric agent can be selected to provide a determined color change at the preselected threshold.

It is noted that the optical density of the changed color of the ketone body indicator may be observed, i.e., visually identified by human vision or compared with a table of known color changes, such as shown in FIG. 10. Alternatively or additionally, the optical density of the changed color may be observed by a computing device, such as a smart phone. For example, the computing device may capture an image of the ketone body indicator such as with a camera, and provide a computer readable comparison of the ketone body indicator with a predetermined indicator. Some embodiments can enhance observation of the colorimetric agent optical change by, for example, increasing optical density by using thicker paper or use of polymeric base to increase thickness of a sensor layer coating, or the use of binding agents such as hydroxypropyl cellulose (see, e.g., U.S. Pat. No. 8,574,896).

As may be understood, the ketone body indicator, collection indicator, and other indicators may use the technique of FIGS. 9 and 10, or similar techniques measuring other compounds, to provide a visual indication or machine readable indication of measured values.

Figure 11:
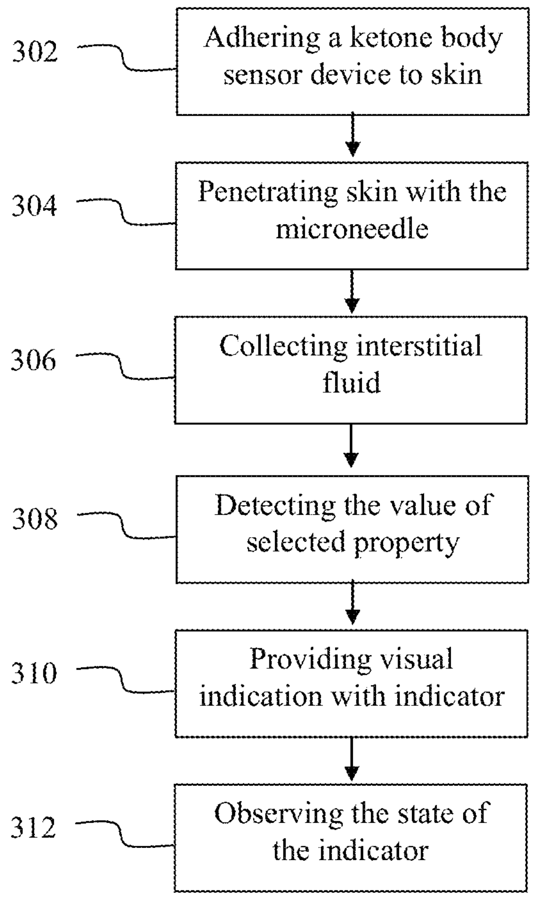
FIG. 11 is flow chart illustrating an exemplary method for using a ketone body indicator, such as for detecting ketosis in an individual, in accordance with one or more embodiments.

FIG. 11 is flow chart illustrating an exemplary method 300 for using a ketone body indicator, such as for detecting ketosis in an individual. As shown, the method 300 includes adhering a ketone body sensor device to skin of the individual at action 302. The method 300 includes penetrating the skin of the individual with the microneedle or microneedles at action 304, after or coincidental with adhering the ketone body sensor device to skin in action 302.

The method 300 further includes collecting interstitial fluid from the microneedle at action 306. Specifically, as described above, interstitial fluid may be drawn along a flow path via capillary forces into contact with the indicators provided in the ketone body sensor device.

The method 300 further includes detecting the value (or values) of a selected property (or properties) of the interstitial fluid at action 308 (e.g., level of ketone bodies). For example, the method 300 includes detecting that a sample amount of the interstitial fluid has been collected with the collection indicator and detecting a ketone body in the interstitial fluid with the ketone body indicator. In embodiments in which the device includes a glucose sensor, action 308 may include detecting a glucose level in the interstitial fluid with the glucose sensor. In embodiments in which the device includes a pH sensor, action 308 may include detecting a pH level in the interstitial fluid with the pH sensor.

As shown in FIG. 11, the method 300 further includes providing a visual indication of the detected value with the device at action 310. Specifically, the collection indicator provides a visual indication that the sample amount has been collected and the ketone body indicator indicates whether the threshold amount of ketone body is present in the sample amount. Optionally, glucose indicator and pH indication, and other indicators, also provide a visual indication reflective of the measured property.

The method 300 further includes observing the state of the indicator after the visual indication is provided, at action 312. For example, the method 300 includes observing the positive or negative state of the ketone body indicator after the visual indication is provided. Optionally, the method 300 includes observing the state or value of the glucose sensor, pH sensor, or other indicators.

In certain embodiments, the indicators may be observed by human eyesight. Further, the observation may include comparison of the indicator with a chart or library of other indicator states, e.g., colors. In other embodiments, an indicator may by observed by capturing an image of the indicator with a computing device so as provide a computer readable comparison of the indicator with a predetermined indicator state, such as color.

For the sake of brevity, conventional techniques related to glucose sensing and/or monitoring, computing including image capture and comparison and other functional aspects of the subject matter may not be described in detail herein. In addition, certain terminology may also be used in the herein for the purpose of reference only, and thus is not intended to be limiting.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A device for detecting a ketone body comprising beta-hydroxybutyrate, the device comprising: a collection apparatus for collecting a sample amount of interstitial fluid, wherein the collection apparatus comprises at least one hollow microneedle for penetrating skin of an individual; a collection layer including a collection port that is in fluid communication with the microneedle; a sensor layer directly on the collection layer wherein the sensor layer contains a feed channel that runs in a longitudinal direction of the device and is in fluid communication with the collection port of the collection layer such that the interstitial fluid may flow from the collection port into the feed channel; at least one fluidic capillary channel on the sensor layer in fluid communication with the feed channel and perpendicular to the feed channel; the at least one fluid capillary channel connects the feed channel to a ketone body indicator having an initial negative state and a positive state when at least a threshold value of a ketone body is collected from the interstitial fluid; a collection indicator in and/or on the sensor layer having an initial state before being contacted with the interstitial fluid and a completed state when contacted by the interstitial fluid, wherein the sensor layer includes hydrophilic and hydrophobic regions adapted to modulate the flow of interstitial fluid through the device.

2. The device of claim 1, wherein the ketone body indicator comprises: an enzyme that catalyzes a reaction of the ketone body; an enzyme cofactor; and a colorimetric agent exhibiting a first optical property and configured to change to a second optical property, different from the first optical property, when the threshold value of the ketone body is collected in the sample amount.

3. The device of claim 1, wherein the ketone body indicator comprises: an enzyme that catalyzes a reaction of ketone body; an enzyme cofactor that is reduced to a reduced cofactor form during the reaction of the ketone body: an electron mediator; and a colorimetric agent that is reduced to a visible compound during oxidation of the reduced cofactor form in the presence of the electron mediator.

4. The device of claim 3, wherein the enzyme is 3-hydroxybutyrate dehydrogenase; the enzyme cofactor is nicotinamide adenine dinucleotide (NAD+); the electron mediator is selected from mPMS (1-Methoxy-5-methylphenazinium), potassium ferricyanide, and 1,10-phenanthroline; and the colorimetric agent is a water soluble tetrazolium (WST).

5. The device of claim 3, wherein the ketone body indicator further comprises: a co-enzyme; and an enzyme stabilizer.

6. The device of claim 1, further comprising a cover layer, wherein the cover layer comprises a window that allows viewing of the ketone body indicator and has a color comparison chart.

7. A patch including the device of claim 1, the patch further comprising an adhesive layer adapted to bond to skin of an individual; the collection layer disposed over the adhesive layer, a sensor layer disposed over the collection layer, and a cover layer disposed over the sensor layer, wherein the cover layer comprises a window that allows viewing of the ketone body indicator in the sensor layer.

8. The patch of claim 7, wherein the adhesive layer comprises a gap surrounding the at least one hollow microneedle.

9. The patch of claim 7, further comprising a cover layer, wherein the cover layer comprises a window that allows viewing of the ketone body indicator and has a color comparison chart.

* * * * *